(12) United States Patent
Reinecke et al.

(10) Patent No.: US 7,465,293 B2
(45) Date of Patent: Dec. 16, 2008

(54) SYRINGE FOR INDUCING THERAPEUTICALLY-EFFECTIVE PROTEINS

(75) Inventors: Julio Reinecke, Köln (DE); Hans Meijer, Köln (DE); Peter Wehling, Düsseldorf (DE)

(73) Assignee: Orthogen Gentechnologie GmbH, Dusseldorf (DE)

( * ) Notice: Subject to any disclaimer, the term of this patent is extended or adjusted under 35 U.S.C. 154(b) by 1014 days.

(21) Appl. No.: 10/378,175

(22) Filed: Mar. 3, 2003

(65) Prior Publication Data

US 2004/0156823 A1 Aug. 12, 2004

Related U.S. Application Data

(62) Division of application No. 09/485,836, filed as application No. PCT/EP98/04866 on Jul. 6, 2000, now Pat. No. 6,623,472.

(30) Foreign Application Priority Data

Aug. 16, 1997 (DE) .................. 197 35 537
May 20, 1998 (EP) .................. 98109186

(51) Int. Cl.
*A61M 5/00* (2006.01)
(52) U.S. Cl. .................................... 604/187

(58) Field of Classification Search ................. 604/506, 604/507, 511, 512, 522, 181–182, 187, 199, 604/200–201, 205, 218, 244, 256, 263, 264, 604/403, 416, 4.01, 6.15, 6.16; 424/85.2, 424/130.1, 134.1
See application file for complete search history.

(56) References Cited

U.S. PATENT DOCUMENTS

| 3,960,139 | A | * | 6/1976 | Bailey | 600/575 |
| 4,118,315 | A | | 10/1978 | Fletcher et al. | |
| 4,553,553 | A | * | 11/1985 | Homann et al. | 600/562 |
| 5,151,192 | A | * | 9/1992 | Matkovich et al. | 210/646 |
| 5,338,312 | A | * | 8/1994 | Montgomery | 604/230 |
| 5,411,488 | A | * | 5/1995 | Pagay et al. | 604/218 |
| 5,411,489 | A | * | 5/1995 | Pagay et al. | 604/218 |
| 5,413,563 | A | * | 5/1995 | Basile et al. | 604/218 |
| 5,789,376 | A | * | 8/1998 | Hsia | 514/6 |

FOREIGN PATENT DOCUMENTS

| GE | 0 088 971 | 3/1983 |
| WO | WO 89/10974 | 11/1989 |

* cited by examiner

*Primary Examiner*—Nicholas D Lucchesi
*Assistant Examiner*—Christopher D Koharski
(74) *Attorney, Agent, or Firm*—Bateman IP Law Group

(57) ABSTRACT

A syringe for inducing therapeutically-effective proteins includes a syringe and an inner structure having an inductor disposed thereon for encouraging development of a desired protein.

27 Claims, 1 Drawing Sheet

SYRINGE FOR INDUCING THERAPEUTICALLY-EFFECTIVE PROTEINS

RELATED APPLICATIONS

The present invention is a divisional of U.S. patent application Ser. No. 09/485,836, filed Jul. 6, 2000 now U.S. Pat. No. 6,623,472, a U.S. Phase Nationalization of PCT/EP98/04866, filed Aug. 5, 1998, which claims priority to European Patent Application 98109186.1, filed May 20, 1998 and German Patent Application 19735537.4, filed Aug. 16, 1997.

This invention relates to a method for producing therapeutically-effective proteins as well as the mean used therein, in particular syringes.

BACKGROUND OF THE INVENTION

Therapeutically-effective proteins, such as erythroproietin, insulin or interferon, have been known for a long time. Many of these proteins are already registered drugs and accordingly are commonly used. Because of the high cost connected with the development and registration of these medications, there is however a need for simple and inexpensive alternatives for the preparation of therapeutically-effective proteins. In addition, not all therapeutically-effective proteins are registered drugs. However, there nevertheless frequently is the requirement to administer these proteins as well to patients. Of particular importance in this context are autologous, that is intrinsic, body proteins because of their presumed good bodily tolerance. Among these proteins are interleukin 1 receptor antagonist, interleukin-4, interleukin-10 and tumour necrosis factor receptor Type I or Type II.

The stimulation of monocytes by adherent immunoglobulin G for the formation of interleukin 1 receptor antagonists is described by Arend and Leung in Immunological Reviews (1994) 139, 71-78 and Moore et al. in Am. J. Respir. Cell Mol. Biol. (1992) 6, 569-575. Andersen et al., in Autoimmunity (1995) 22, 127-133, explained that the therapeutic effect of immunoglobulin G to be observed in vivo cannot be put down to an intensified formation of interleukin 1 receptor antagonist, and that the in vitro formation of interleukin 1 receptor antagonist (IRAP, IL-lra) occurs by means of monocytes in dependence on serum and plasma components absorbed in polypropylene. Methods of product IL-lra directly usable in therapy are not described in these publications.

The underlying technical problem of this invention therefore consists in providing a method and means for preparing therapeutically-effective proteins which serve as inexpensive and rapidly implemented alternatives to the use and preparation of conventional drug preparations.

SUMMARY OF THE INVENTION

The invention solves this problem by providing a method for preparing at least one therapeutically-effective protein or a protein mixture in a syringe, in which the inner structures of the syringe are coated with inductors, in particular immunoglobulins, the syringe is filled with a body fluid of a patient, incubated and the therapeutically-effective protein is formed in the body fluid. The invention therefore provides in a first procedure step that the inner structures of the syringe are coated with inductors, in particular immunoglobulins, and these are fixed there. After coating, the syringe is filled in a second procedure step with a body fluid, in particular blood, lymph fluid, saliva or urine, and incubated. Preferably the body fluid is taken with the syringe directly from the patient. The inductors fixed to the inner structures of the syringe, in particular immunoglobins, induce specifically in the body fluid, i.e. depending on the inductor used, in particular immunoglobulin, and the body fluid used, the formation of therapeutically-effective proteins which are accordingly accumulated, or that is to say formed in the body fluid in the syringe. The body fluid accumulated in this way can be stored in sterile conditions in the syringe and resupplied as or when required to the patient directly without additional treatment or for example after centrifuging and/or sterile filtration.

The invention also provides that the formation of several proteins is induced simultaneously in a body fluid, so that a body fluid is formed which has a raised concentration of several proteins.

In the context of this invention, an inner structure of a syringe is taken to mean any area or any structure of the syringe, which inner structure is inside the syringe and which comes into contact with the body fluid to be contained and which can be coated with inductors, in particular immunoglobulins. Particularly advantageous is the inner structure of a syringe whose inner surface optionally in a surface with a structure for expanding the surface area. The inner structure can however be formed either alternatively or additionally by particles, spheres, gels, glass wool, granulated material or similar, in order to make available a greater surface area for the inductors, in particular immunoglobulins.

In a particularly advantageous design of the invention, provision is made for the syringe, in particular the inner structure of the syringe, to be made of polystyrene, polypropylene, glass or a similar material, i.e. consists of these materials or essentially contains these materials, so long as this material possesses inductor-binding, in particular immunoglobulin-binding, properties, that is to say adhesion of the inductors, in particular immunoglobulins, is possible. A preferred form of implementation of the invention provides for the production of the inner structure of the syringe, while the inherently non-protein-binding inner structure of the syringe is provided with a protein-binding coating.

This invention is advantageous inasmuch as that an easily implemented method is provided, by which autologous therapeutically-effective proteins, capable of preparation by induction, in particular immunoglobulin induction, can be prepared and in the form prepared this way, i.e. together with the other components of the body fluids in the syringe, can be administered directly to the patient, i.e. without further manipulation such as transfer to another container, for example. If necessary, centrifuging and/or sterile filtration can be provided for separating solid components. The use of commercially available and often expensive drugs is therefore unnecessary. Furthermore, the use of therapeutically-effective autologous proteins is possible which until now have not been legally authorised drugs and therefore not legally available. Finally the invention, which is based on the drug preparation taking place outside the patient, provides to be advantageous in that contamination, impurities, infection or similar of the therapeutically-effective proteins, are avoided.

In a particularly preferred form of implementing this invention, the therapeutically-effective protein is interleukin 4, interleukin 10 or soluble tumour necrosis factor receptor Type I or Type II, especially preferred being interleukin 1 receptor antagonist (or IL-lra).

In another especially preferred form of implementing this invention, immunoglobulin G is the immunoglobulin with which the inner structure of the syringe is coated. In the context of this invention, immunoglobulin G is understood to mean isolated immunoglobulin G but also immuno-complexes containing immunoglobulin G, preparations containing immunoglobulin G such as sera, plasma or immunoglobulin G Fc fragment, or preparations or complexes containing the latter.

This invention therefore provides, in a particularly preferred form of implementation, for a method of preparing interleukin 1 receptor antagonists, whereby the inner structure of a syringe is coated with an inductor, in particular an immunoglobulin, and especially preferred immunoglobulin G, the syringe is filled with a body fluid, preferably blood, is incubated and the interleukin 1 receptor antagonist is formed and accumulated in the body fluid. Through the binding or adhesion of the inductor, in particular immunoglobulin G, on the surface of the inner structure of the syringe, the latter is in a position to stimulate the monocytes in the blood to form interleukin 1 receptor antagonist, so that this is accumulated in the blood. After incubation, i.e. after accumulation of the interleukin 1 receptor antagonist, the blood in the syringe can be supplied without further manipulation, such as transferring into another container for example, directly to the patient from whom the blood put into the syringe had been taken. For separation of solid components, such as cell, centrifuging and/or sterilisation can be advantageously provided. The invention therefore also provides that the blood can be taken from the patient by means of the inductor-coated, in particular immunoglobulin G-coated, syringe the blood can be incubated in the syringe and, after IL-lra formation, can be supplied to the patient again with the syringe. Such a procedure is, for example, especially advantageous in the field of neuro-orthopaedics, i.e. for example in the case of neurologically-caused back complaints. Hitherto only an intervertebral disc operation, cortisone treatments, irrigation procedures using saline solutions or similar, were considered for the treatment of this type of complaint. This invention now allows the simple and inexpensive provision of a therapeutically-effective protein for treating these complaints.

In another preferred form of implementation, the invention provides that the inner structure of the syringe is coated additionally with anticoagulants, in particular heparin. According to the invention, the anticoagulants can also be provided not as a coating but to be introduced uncombined in the container, for example to be put into the syringe in the dry frozen or liquefied state.

In another preferred form of implementation, the invention provides for the incubation of the body fluid in the syringe over a period of 12 to 72 hours, preferably carried out at an ambient temperature up to 41° C., in particular 37° C.

In one form of the invention, the invention also provides that after the formation of the therapeutically-effective protein in the body fluid, the body fluid is further processed in order to separate for example certain components of the latter, for example blood plasma or blood platelets. This separation process can be performed, in a preferred form of implementation of the invention, by centrifuging.

In a further form of implementation, the invention concerns a method of producing a syringe, suitable for in vitro induction of interleukin 1 receptor antagonists, in which an inductor, preferably an immunoglobulin, in particular immunoglobulin G, is placed in the syringe with a protein-binding inner structure and incubated so that the inductor, in particular the immunoglobulin G, binds to the inner structure.

It is self-evident that the invention also concerns the syringe produced in this way, which is manufactured in a particularly preferred form of implementation from polystyrene, polypropylene or glass, the syringe being distinguished by a coating of its inner structure with an inductor, in particular with an immunoglobulin, preferably with immunoglobulin G.

The invention also relates to the use of immunoglobulin, in particular immunoglobulin G, for coating the inner structures of syringes, preferably made of polystyrene, polypropylene or glass, for the in-vitro induction of therapeutically-effective proteins, preferably interleukin 1 receptor antagonists.

Additional advantageous forms of the invention emerge from the sub-claims.

BRIEF DESCRIPTION OF THE DRAWING

The invention is explained in more detail with reference to figures and examples of implementation.

DETAILED DESCRIPTION OF THE INVENTION

EXAMPLE 1

Figure 1:
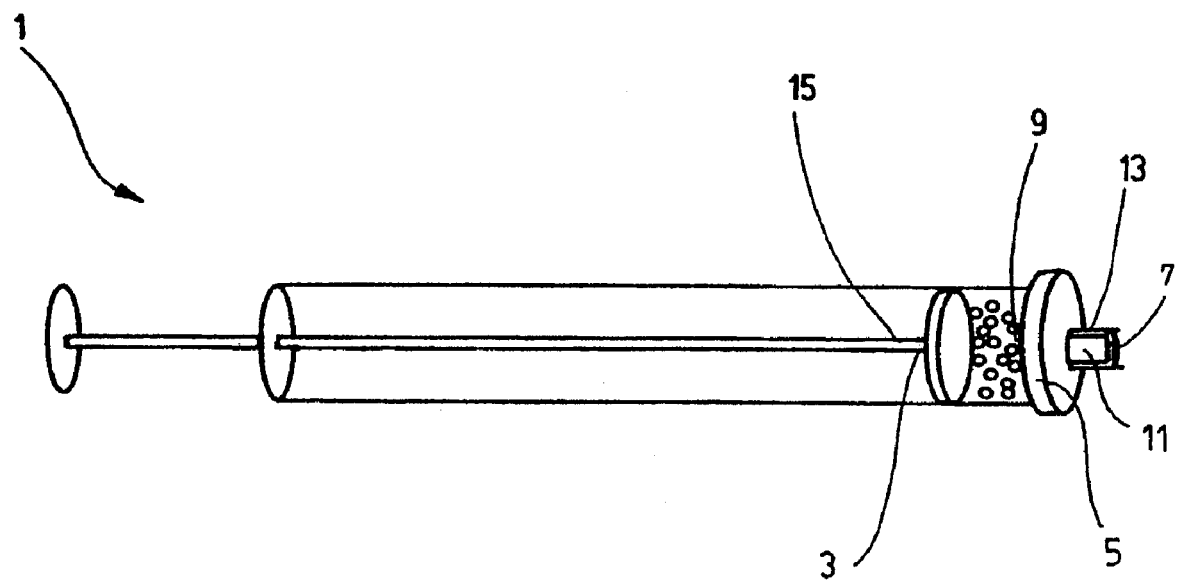
FIG. 1. shows a schematic representation of a syringe according to the invention.

FIG. 1 shows a syringe 1 made of polystyrene with a piston 3, a sealing cap 5 (which can be unscrewed) with a cap extension 13 (made Luer) and a removable cap 7 with a septum arranged on, and blanking off, the cap extension 13. The piston 3 has a predetermined breaking point 15. Also shown is granulated material 9 made of polystyrene coated with IgG (not represented). The size of the granulated particles 9 is between 1 and 3 mm diameter, though smaller particles, in particular larger than 100 µm also can be used.

To prepare the syringe 1, the granulated material 9 is coated with a commercially available IgG preparation (Venimmun®, Behring), while the IgG preparation is taken into the syringe and the granulated material as well as the syringe inner wall is moistened by the IgG preparation. Then the syringe 1 is incubated at ambient temperature for at least 15 minutes, in order to ensure a complete bond with the granulated material 9 and the syringe inner wall. Finally heparin (liquemin N 2500, heparin sodium 2500 I.E.) or citrate (ACDA) is put in the syringe so as to prevent coagulation of the blood to be taken in later.

The syringe 1 is used, while blood of patient is taken with the aid of an adapter (not shown), which connects the removable cap 7 with a cannula (not shown) by means of a flexible tube (not shown). The adapter has a needle, by means of which the septum in the cap extension 13 is pierced. Then the adapter is removed and incubation of the complete blood carried out at 37° C. for 24 hours protected by the removable cap 7, whose septum has automatically sealed itself. Incubation can occur in a vertical or horizontal position. If incubation is carried out in the vertical position, the plasma is removed through the septum and a sterile filter attachment (0.2 µm). Additionally or alternatively, a centrifuging process can be provided. If incubation is carried out in the horizontal position, the blood is centrifuged and the plasma removed through a sterile filter attachment (0.2 µm). However, provision can be made for the plasma to be removed through the septum without carrying out centrifuging. The plasma is then reinjected, for example, in a nerve ending or joint of the patient.

EXAMPLE 2

Syringe With Granulated Material

Sterile granulated material made of polystyrene, glass or another non-pyrogenic protein-binding material is coated with protein (for example an IgG preparation registered under AMG (e.g. Venimmun®, Behring) under sterile conditions in a hatch process in sterile water or aqueous buffer diluted to 10 to 100 µm/ml) and then dried.

A conventional polypropylene syringe (5, 10, 20 or 50 ml) is filled with the protein-coated granulated material (1, 2, 4 or 10 cm³) as well as with a sufficient quantity of an anticoagulant such as heparin (liquemin, heparin sodium 2500 I.E.) or citrate (for example ACDA).

The filled syringe is packaged including receiving cannula and flexible tube and then sterilised by gamma radiation or electron [sic] radiation. This ensures a pyrogen-free product.

The user removes the sterile instrument set and takes blood from the patient. At its opening in the cap extension above, the syringe has a septum which is pierced by the receiving attachments, that is the needle of the adapter, for the taking of the blood. After removal of the adapter, the septum automatically reseals itself. The syringe piston is broken off at a predetermined breaking point after taking the blood.

The syringe with blood is incubated for 24 hours at 37° C. to 41° C.

a) If the incubation is carried out in the vertical position, the plasma is removed through the septum and a sterile filter attachment, for example 0.2 µm.

b) If the incubation is carried out in the horizontal position, the plasma is removed through a sterile filter attachment, for example 0.2 µm after centrifuging the syringe.

Reinjection of the plasma is carried out, for example, at a nerve ending, in the joint or in the intervertebral disc.

EXAMPLE 3

Syringe Without Granulated Material

A syringe made of a non-pyrogenic protein-binding material (5, 10, 20 or 50 ml) is coated in sterile conditions with protein (for example a commercial IgG preparation registered under AMG (e.g. Venimmun®, Behring)), if necessary in sterile water or aqueous buffer diluted to 10 to 100 µm/ml). Preferably the syringe is made of polystyrene, glass or a specially modified other material.

The coated syringe is filled with a sufficient quantity of heparin (liquemin, heparin sodium 2500 I.E.) or citrate (ACDA).

The coated and filled syringe, including receiving cannula and flexible tube is then sterilised by gamma radiation or electron [sic] radiation. This ensures a pyrogen-free product.

The user removes the sterile instrument set and takes blood from the patient. Contained in the cap extension at the opening above, the syringe has a septum which is pierced by the receiving attachments, that is the needle of the adapter, for the taking of the blood. After removal of the adapter, the septum automatically reseals itself. The syringe piston is broken off at a predetermined breaking point after taking the blood.

The syringe with blood is incubated for 24 hours at 37° C. to 41° C.

a) If the incubation is carried out in the vertical position, for example in a test tube stand, the plasma is removed through the septum and filtration carried out through a sterile filter attachment, for example 0.2 µm.

b) If the incubation is carried out in the horizontal position, after centrifuging the syringe the plasma is removed through the septum, in the process a filtration being carried out through a sterile filter attachment, for example 0.2 µm.

Reinjection of the plasma is carried out, for example, at a nerve ending, in the joint or in the intervertebral disc.

EXAMPLE 4

Preparation of Interleukin 1 Receptor Antagonists in a Syringe Using Heparin

A commercially available and legally authorised drug immunoglobulin G preparation (Venimmun®, Behring) is diluted in a sterile aqueous buffer to 10 to 100 µg/ml.

This solution is filled in to a sterile syringe made of polystyrene, whose inner surface effectively binds protein. Then an incubation of at least 15 minutes is carried out at ambient temperature to saturate the inner wall surface with the immunoglobulin G. The incubation period can also be more than 24 hours.

After completing the incubation, and therefore after adhesion of the immunoglobulin G in the inner surface of the syringe, the immunoglobulin G solution is removed from the syringe and the syringe is temporarily stored in sterile conditions. A legally authorised drug heparin (liquemin, heparin sodium 2500 I.E.), acting as an anticoagulant, is drawn up into the coated syringe.

Using the coated syringe, venous blood is subsequently taken from the patient in sterile conditions.

The syringe is incubated at ambient temperature for 12 to 72 hours. In this time a large accumulation of the proteins, in particular the interleukin 1 receptor antagonists, contained in the plasma, occurs in the blood plasma. A concentration of 1 to 50 ng/ml of the interleukin 1 receptor antagonists could be determined.

Then, using the coated syringe, the blood or the plasma is injected into the patient.

EXAMPLE 5

Preparation of the Interleukin 1 Receptor Antagonists in a Syringe

A commercially available and legally authorised drug immunoglobulin G preparation (Venimmun®, Behrin) is diluted in a sterile aqueous buffer to 10 to 100 µg/ml.

This solution is filled into a sterile syringe made of polystyrene, whose wall material effectively binds protein. Incubation is carried out at ambient temperature over at least 15 minutes, which servers to saturate the inner wall surface with the immunoglobulin G.

After completing the incubation and adhesion of the immunoglobulin G to the inner surface of the syringe, the immunoglobulin G solution is removed and the syringe is temporarily stored in sterile condition.

Using the coated syringe, venous blood is subsequently taken from the patient in sterile conditions.

The syringe is incubated at ambient temperature for 12 to 24 hours. In this time a large accumulation of the proteins, in particular the interleukin 1 receptor antagonists, contained in the plasma, occurs in the blood plasma. A concentration of 1 to 50 ng/ml of the interleukin 1 receptor antagonists could be determined.

Then using the coated syringe, the blood or the plasma is injected into the patient.

The invention claimed is:

1. A syringe with an inner structure consisting of at least one of the group consisting of materials containing polystyrene and materials containing glass, the inner structure being coated with an inductor, wherein the inner structure is coated with the inductor independent of introduction of a body fluid into the syringe;

wherein the inductor is selected to induce formation of a therapeutically effective protein within a body fluid once the body fluid is introduced into the syringe, and wherein the therapeutically effective protein is therapeutically effective for treatment when the protein is introduced into a body; and wherein the inductor is immunoglobulin G.

2. The syringe according to claim 1, further comprising anticoagulants disposed in the syringe independent of the introduction of a body fluid into the syringe.

3. The syringe according to claim 1, further comprising a body fluid disposed in the syringe.

4. The syringe according to claim 1, further comprising blood disposed in the syringe.

5. The syringe according to claim 1, wherein the therapeutically-effective protein is selected from the group consisting of interleukin 1 receptor antagonist (IRAP), interleukin 4, interleukin 10 and soluble tumour necrosis factor receptor Type I or Type II.

6. A syringe with an inner structure consisting of at least one of the group consisting of materials containing polystyrene and materials containing glass, the inner structure being coated with an inductor, wherein the inner structure is coated with the inductor independent of introduction of a body fluid into the syringe;

wherein the inductor is selected to induce formation of a therapeutically effective protein within a body fluid once the body fluid is introduced into the syringe, and wherein the therapeutically effective protein is therapeutically effective for treatment when the protein is introduced into a body;

wherein the syringe further comprises a therapeutically-effective protein disposed in the syringe independent of the introduction of a body fluid into the syringe; and wherein the therapeutically-effective protein is selected from the group consisting of interleukin 1 receptor antagonist (IRAP), interleukin 4, interleukin 10 and soluble tumour necrosis factor receptor Type I or Type II.

7. The syringe according to claim 1, wherein the inner structure comprises at least one of the group consisting of spheres, gels, glass wool, granulated material and particles.

8. A syringe with an inner structure consisting of at least one of the group consisting of materials containing polystyrene and materials containing glass, the inner structure being coated with an inductor, wherein the inner structure is coated with the inductor independent of introduction of a body fluid into the syringe;

wherein the inductor is selected to induce formation of a therapeutically effective protein within a body fluid once the body fluid is introduced into the syringe, and wherein the therapeutically effective protein is therapeutically effective for treatment when the protein is introduced into a body; and wherein the inductor comprises immunoglobulin, and wherein the therapeutically-effective protein is selected from the group consisting of interleukin 1 receptor antagonist (IRAP), interleukin 4, interleukin 10 and soluble tumour necrosis factor receptor Type I or Type II.

9. The syringe according to claim 8, further comprising anticoagulants disposed in the syringe independent of the introduction of a body fluid into the syringe.

10. A syringe comprising:
an inductor; and
an inner structure comprising at least one of the group consisting of spheres, gels, glass wool, granulated material and particles disposed in the syringe, with the inductor being disposed on said inner structure, wherein the inductor is disposed on said inner structure independent of introduction of a body fluid into the syringe;

wherein the inductor is selected to induce formation of a therapeutically effective protein within a body fluid once the body fluid is introduced into the syringe, and wherein the therapeutically effective protein is therapeutically effective for treatment when the protein is introduced into a body; and wherein the inductor is immunoglobulin IgG.

11. The syringe according to claim 10, further comprising a therapeutically-effective protein disposed in the syringe independent of the introduction of a body fluid into the syringe.

12. The syringe according to claim 11, further comprising anticoagulants disposed in the syringe independent of the introduction of a body fluid into the syringe.

13. The syringe according to claim 11, further comprising a body fluid disposed in the syringe.

14. The syringe according to claim 11, wherein the therapeutically-effective protein is at least one of the group consisting of interleukin 1 receptor antagonist (IRAP), interleukin 4, interleukin 10 and soluble tumour necrosis factor receptor Type I or Type II.

15. The syringe according to claim 10, further comprising anticoagulants disposed in the syringe independent of the introduction of a body fluid into the syringe.

16. The syringe according to claim 10, further comprising a body fluid disposed in the syringe.

17. A syringe comprising:
an inductor; and
an inner structure comprising at least one of the group consisting of spheres, gels, glass wool, granulated material and particles disposed in the syringe, with the inductor being disposed on said inner structure, wherein the inductor is disposed on said inner structure independent of introduction of a body fluid into the syringe;

wherein the inductor is selected to induce formation of a therapeutically effective protein within a body fluid once the body fluid is introduced into the syringe, and wherein the therapeutically effective protein is therapeutically effective for treatment when the protein is introduced into a body; and wherein the therapeutically effective protein is selected from the group consisting of interleukin and soluble tumor necrosis factor.

18. A syringe comprising:
an inner structure configured to contact a fluid which is disposed in the syringe; and
an inductor, the inductor disposed as a coating on the inner structure, the inductor being present on the inner structure independent of the introduction of a body fluid into the syringe;

wherein the inductor is configured to induce production of a therapeutically effective protein in a body fluid once the body fluid is introduced into the syringe, and wherein the protein is therapeutically effective for treatment when the protein is introduced into a body; and wherein the protein is a type I or type II tumor necrosis factor receptor.

19. The syringe according to claim 18, wherein the inductor is immunoglobulin.

20. The syringe according to claim 18, wherein the inductor is immunoglobulin IgG.

21. The syringe according to claim 18, further comprising an anticoagulant disposed in the syringe independent of the introduction of a body fluid into the syringe.

22. A syringe comprising:
an inner structure configured to contact a fluid which is disposed in the syringe; and
an inductor, the inductor disposed as a coating on the inner structure, the inductor being present on the inner structure independent of the introduction of a body fluid into the syringe;
wherein the inductor is configured to induce production of a therapeutically effective protein in a body fluid once the body fluid is introduced into the syringe, and wherein the protein is therapeutically effective for treatment when the protein is introduced into a body; and
wherein the therapeutically effective protein is an interleukin.

23. The syringe according to claim 22, wherein the therapeutically effective protein is interleukin 4.

24. The syringe according to claim 22, wherein the therapeutically effective protein is interleukin 10.

25. A syringe comprising:
an inner structure configured to contact a fluid which is disposed in the syringe; and
an inductor, the inductor disposed as a coating on the inner structure, the inductor being present on the inner structure independent of the introduction of a body fluid into the syringe;
wherein the inductor is configured to induce production of a therapeutically effective protein in a body fluid once the body fluid is introduced into the syringe, and wherein the protein is therapeutically effective for treatment when the protein is introduced into a body; and
wherein the therapeutically effective protein is interleukin 1 receptor antagonist.

26. A syringe with an inner structure consisting of at least one of the group consisting of materials containing polystyrene and materials containing glass, the inner structure being coated with an inductor, wherein the inner structure is coated with the inductor independent of introduction of a body fluid into the syringe;
wherein the inductor is selected to induce formation of a therapeutically effective protein within a body fluid once the body fluid is introduced into the syringe, and wherein the therapeutically effective protein is therapeutically effective for treatment when the protein is introduced into a body; and
wherein the therapeutically-effective protein is selected from the group consisting of interleukin 1 receptor antagonist (IRAP), interleukin 4, interleukin 10 and soluble tumour necrosis factor receptor Type I or Type II.

27. A syringe comprising:
an inner structure configured to contact a fluid which is disposed in the syringe; and
an inductor, the inductor disposed as a coating on the inner structure, the inductor being present on the inner structure independent of the introduction of a body fluid into the syringe;
wherein the inductor is configured to induce production of a therapeutically effective protein in a body fluid once the body fluid is introduced into the syringe, and wherein the protein is therapeutically effective for treatment when the protein is introduced into a body; and
wherein the inductor is immunoglobulin.

* * * * *

UNITED STATES PATENT AND TRADEMARK OFFICE
CERTIFICATE OF CORRECTION

PATENT NO. : 7,465,293 B2  Page 1 of 1
APPLICATION NO. : 10/378175
DATED : December 16, 2008
INVENTOR(S) : Julio Reinecke It is certified that error appears in the above-identified patent and that said Letters Patent is hereby corrected as shown below:

Title Page: item (63):

On the front page of the patent under the section "Related U.S. Application Data":
it reads "Division of applicaiton No. 09/485,836, filed as application No. PCT/EP98/04866 on Jul. 6, 200, now Pat. No. 6,623,472."; it should read --Division of application No. 09/485,836, filed Jul. 6, 2000, now Pat. No. 6,623,472, which is the national stage entry of PCT/EP98/04866 filed Aug. 5, 1998.--

Column 2:
line 20, it reads "...inner surface optionally in..."; it should read --...inner surface optionally has...--

Column 4:
line 12, it reads "figures and examples..."; it should read --the figure and examples...--

Column 6:
line 44, it reads "minutes, which servers to saturate..."; it should read --minutes, which serves to saturate...--

Signed and Sealed this

Twenty-fourth Day of March, 2009

JOHN DOLL
*Acting Director of the United States Patent and Trademark Office*